United States Patent [19]
Matsuura et al.

[11] Patent Number: 5,246,637
[45] Date of Patent: Sep. 21, 1993

[54] METHOD FOR PRODUCING ELECTRET FILTER

[75] Inventors: Satoshi Matsuura; Akira Yokoyama; Yoshio Shinagawa, all of Kuga, Japan

[73] Assignee: Mitsui Petrochemical Industries, Ltd., Tokyo, Japan

[21] Appl. No.: 877,103

[22] Filed: May 1, 1992

[30] Foreign Application Priority Data

May 2, 1991 [JP] Japan .................... 3-100765

[51] Int. Cl.$^5$ .................... B29C 35/10; B29C 71/04
[52] U.S. Cl. .................... 264/22; 264/24; 264/154; 264/103; 264/288.8; 264/DIG. 47; 425/174.8 E
[58] Field of Search .................... 264/22, 24, 154, 288.8, 264/DIG. 47, DIG. 48, 103; 425/174.8 E, 174.8 R, 174.6; 55/155

[56] References Cited

U.S. PATENT DOCUMENTS

| | | | |
|---|---|---|---|
| Re. 32,171 | 6/1986 | Turnhout | 264/22 |
| 4,310,478 | 1/1982 | Balslev et al. | 264/22 |
| 4,375,718 | 3/1983 | Wadsworth et al. | 264/22 |
| 4,626,263 | 12/1986 | Inoue et al. | 55/155 |
| 5,112,677 | 5/1992 | Tani et al. | 55/155 |
| 5,143,767 | 9/1992 | Matsuura et al. | 264/22 |

FOREIGN PATENT DOCUMENTS

| | | | |
|---|---|---|---|
| 56-85475 | 7/1981 | Japan | 264/22 |
| 60-126372 | 7/1985 | Japan | 264/22 |
| 61-289177 | 12/1986 | Japan | 264/22 |

*Primary Examiner*—Jeffery Thurlow
*Attorney, Agent, or Firm*—Sherman and Shalloway

[57] ABSTRACT

A highly efficient, reliable method is provided for producing an electret filter having an excellent collection efficiency. In this method, a film containing a resin material with high molecular weight is formed and split to form split yarns. The split yarns are then subjected to a charging treatment, and the electret filter is produced from the charged split yarns.

15 Claims, 1 Drawing Sheet

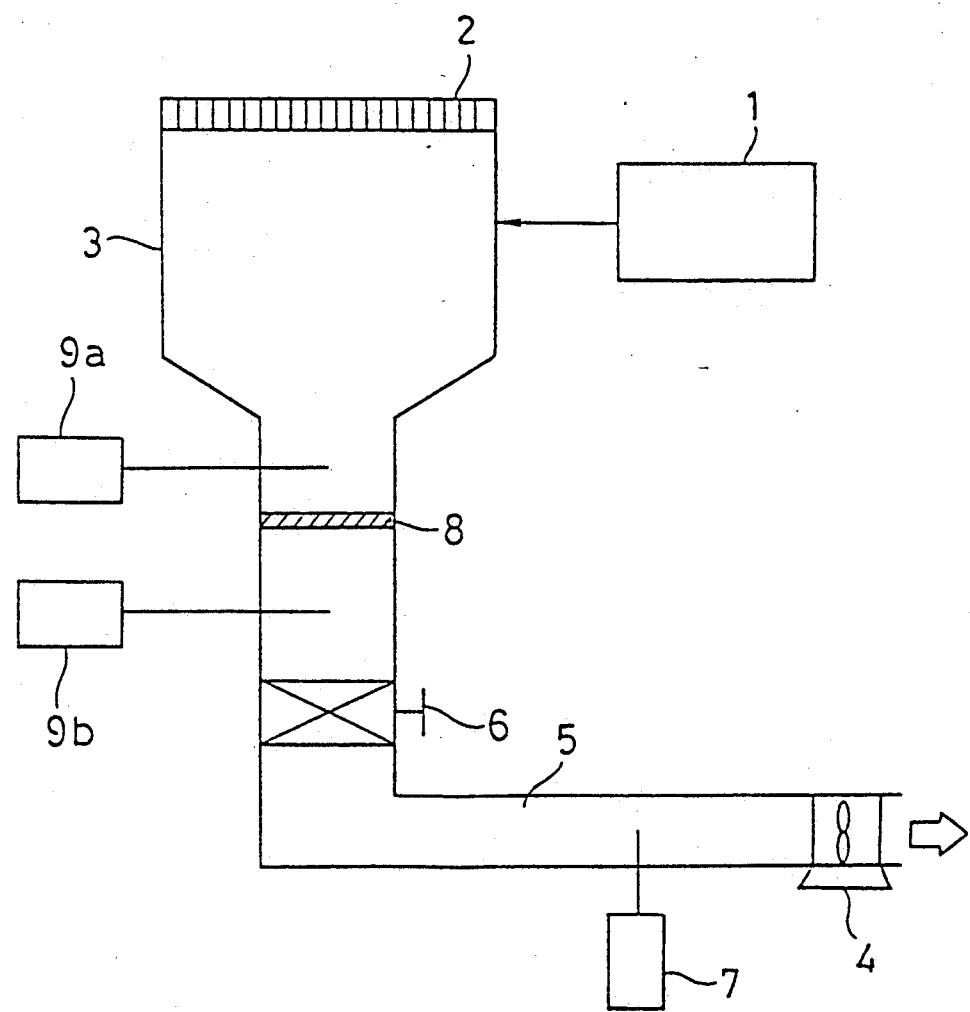

METHOD FOR PRODUCING ELECTRET FILTER

BACKGROUND OF THE INVENTION

This invention relates to a method for producing an electret filter. More particularly, this invention relates to a highly efficient method for producing an electret filter which is capable of collecting fine particles at a high collection efficiency.

In a known method, an electret filter is produced by forming a film of a starting resin material, subjecting the film formed to a homo charging either before or after stretching the film, splitting the charged film to produce split yarns, and collecting the split yarns to form them into a filter of a desired configuration.

Such a method wherein the film splitting step is carried out subsequent to the homo charging of the film suffer from frequent film tearing since the film strength is decreased by the surface oxidation or minute surface irregularities caused by the homo charging.

The homo charging of the film also results in an increased adhesion of the film to electrodes, which may also lead to film tearing. Once the film is torn, the torn film, which has been electrically charged, easily becomes twined on the roll or the like to induce various troubles in the production process.

It is therefore an object of the present invention to provide a reliable, highly efficient, and quick method which is capable of producing an electret filter having various excellent performances including an excellent collection efficiency with no production troubles.

To achieve the above mentioned object, the present invention provides a method for producing an electret filter comprising the steps of forming a film comprising a high molecular weight compound, splitting the film to form split yarns, subjecting the split yarns to a homo charging, and producing the electret filter from the charged split yarns.

BRIEF DESCRIPTION OF THE DRAWING

FIG. 1 is a schematic view of the apparatus used for measuring the collection efficiency of the electret filter produced in accordance with the method of the present invention.

DESCRIPTION OF THE INVENTION

The method for producing an electret filter according to the present invention is described in further detail.

In the method of the present invention, a film is first formed from a starting resin material which may be a polar, non-polar, crystal or amorphous high molecular weight compound or a mixture thereof.

Examples of the non-polar high molecular weight compounds include polyolefins such as polyethylene and polypropylene, polystyrene, polyethylene tetrafluoride, ethylene tetrafluoride-propylene hexafluoride copolymers etc.

Polar high molecular weight compounds include those having within the molecule a polar group selected from, for example, carboxyl group, ester group, amide group, hydroxyl group, ether group, nitrile group, carbonyl group, and a halogen atom such as chlorine atom. Exemplary polar high molecular weight compounds include polyesters such as polyethylene terephthalate and polytetramethylene terephthalate; polyamides such as nylon 6, nylon 66 and nylon 12; polycarbonates; polyacrylates such as polymethyl methacrylate and polyethyl acrylate; acrylonitrile-styrene copolymer resins (AS resins); acrylonitrile-butadiene-styrene copolymer resins (ABS resins); polyvinyl chloride; polyvinylydene chloride; polyethylene trifluoride; polyacetal; polyacrylonitrile; etc.

A modified non polar high molecular weight compounds prepared by graft copolymerizing a monomer having a polar group therein with a non-polar high molecular weight compound may also be used as a polar high molecular weight compound.

Examples of such modified non-polar high molecular weight compounds include those prepared by graft copolymerizing at least one compound selected from unsaturated carboxylic acids and their derivatives with a non-polar high molecular weight compound in the presence of a radical polymerization initiator such as an organic peroxide.

Typical unsaturated carboxylic acids and their derivatives which may be used for the graft modification of the non-polar high molecular weight compounds, include acrylic acid; methacrylic acid; α-ethylacrylic acid; unsaturated dicarboxylic acids such as maleic acid, fumaric acid, itaconic acid, citraconic acid, tetrahydrophthalic acid, methyltetrahydrophthalic acid, endocisbicyclo[2,2,1]hepto-5-en-2,3-dicarboxylic acid (nadic acid), methyl-endocis-bicyclo[2,2,1]hepto-5-en-2,3-dicarboxylic acid (methylnadic acid) etc.; and derivatives of the unsaturated dicarboxylic acids such as acid halides, amides, imides, acid anhydrides, esters of the unsaturated dicarboxylic acids. Illustrative examples of the unsaturated dicarboxylic acid derivatives include maleoyl chloride, maleimide, maleic anhydride, citraconic anhydride, monomethylmaleic acid, dimethylmaleic acid, etc. Such unsaturated carboxylic acids and their derivatives may be used alone or in combination of two or more. Among these, preferred in the method of the present invention are unsaturated dicarboxylic acids and their anhydrides, and most preferred are maleic acid, nadic acid, and their anhydrides.

The modified non-polar high molecular weight compound may generally contain from 0.05 to 15% by weight, and preferably from 0.5 to 3% by weight of the unsaturated carboxylic acid or the derivative thereof. In other words, the modified non-polar high molecular weight compound may have been graft modified to such an extent.

In the present invention, the film may be produced from either single high molecular weight compound, or a mixture of two or more high molecular weight compounds as typified above. When a mixture of two or more high molecular weight compounds are used, it may comprise a mixture of polar high molecular weight compounds, a mixture of non-polar high molecular weight compounds, or a mixture of a polar and a non-polar high molecular weight compounds. The polar high molecular weight compound may partly comprise a modified non-polar high molecular weight compound.

When both the non-polar and the polar high molecular weight compounds are used for the film production, they can be mixed in a weight ratio of the non-polar high molecular weight compound to the polar high molecular weight compound of 60 to 99:0.5 to 39.5, and preferably 80 to 95:1 to 10. When the polar high molecular weight compound partly comprises a modified non-polar high molecular weight compound, the modified non-polar high molecular weight compound may generally comprise about 0.5 to 20% by weight, and preferably about 4 to 10% by weight of the total composition.

The high molecular weight compound used for the film production may optionally contain a heat stabilizer, a weathering stabilizer, an antistatic agent, a slip agent, an anti-blocking agent, a lubricant, an inorganic or organic filler, a dye, a piqment, or the like.

In the method of the present invention, the high molecular weight compound as described above is formed into a film, which is subsequently split to produce net-like split yarns. The split yarns are then subjected to a homo charging to produce electretized split yarns, which are used to form the electret filter.

The film formation from the above described high molecular weight compound may be carried out by any desired conventional process which is generally used to produce a film from such a resin, for example, a blown-film extrusion, slot die extrusion using a T-die, calendering, or the like.

The film formed may have a thickness suitably selected to provide the electret filter product with a desired deposition weight and a pressure loss. The film may generally have a thickness of about 10 to 100 μm, and preferably about 20 to 50 μm in order to enable subsequent optional stretching of the film to 6 to 10 times its length.

The film, after an optional stretching, is split with a splitting mean, for example, a wire fillet roll or a needle-mounted roll to produce the split yarns.

When the film is stretched, the film may be stretched in machine direction at a temperature of not higher than the melting point and higher than the softening point of the high molecular weight compound used to form the film, for example, at a temperature of about 130° to 150° C. by using a roll, a hot plate, an oven, or the like. The film may be generally stretched to about 5 to 10 times its length, and preferably, to about 6 to 8 times its length for retaining fair stability after the stretching and for ease of the subsequent splitting of the stretched film.

The resulting split yarns may be either directly fed to the next step without winding, or wound on a cardboard cylinder or a drum before feeding to the next step.

Next, the split yarn is subjected to the homo charging so that the split yarn becomes an electret. The homo charging may be carried out by any conventional electretizing process. Non-limiting such conventional processes include a thermal electretization wherein the split yarns are heated until the split yarns are softened, and the softened yarns are cooled with a direct high-voltage current being applied to the yarn to electretize the split yarns; an electo-electretization wherein the split yarns are treated on their surfaces with corona discharge or pulse high-voltage current to electretize the split yarns, or wherein the split yarns are held on their major surfaces between dielectrics to apply direct high-voltage current thereto to thereby electretize the split yarns; a radio electretization wherein the split yarns are irradiated with γ rays or electron rays; a mechanoelectretization wherein the split yarns are subjected to plastic deformation by application of a pressure to electretize the split yarns; and an auto-electretization wherein the split yarns are irradiated with light with a voltage being applied to electretize the split yarn. Among the processes as typified above, preferred are the processes wherein the heated or non-heated split yarns are intermittently treated with corona discharge, and the process wherein the split yarns are sandwiched between a pair of needle-shaped electrodes to effect the corona discharge treatment.

In the method of the present invention, the thus charged split yarns are cut to a length of, for example, 90 mm, and fed to an opener to produce an electret raw cotton. The fiber or yarn constituting the electret raw cotton may have any desired size by preliminarily selecting the thickness of the film being split, extent to which the film is to be stretched, degree of the splitting, and the like.

Next, the resulting electret fibers are collected to form them into a desired shape to thereby produce the electret filter.

The electret fibers are formed into the electret filter by weaving, knitting, tufting, or forming into a nonwoven fabric in accordance with a suitable conventional method. Typical methods include needle punching, thermal bonding, ultrasonic bonding, and the like.

The electret filter produced in accordance with the method of the present invention is capable of collecting fine particles of a particle size of, for example, up to 1 μm at a high efficiency, and therefore, quite suitable for use as an air filter, a filter for an air cleaner, a vacuum cleaner or an air conditioner, a mask, or the like.

The present invention is described in further detail by referring to the following non limiting Examples of the present invention and Comparative Examples.

EXAMPLES

Example 1

A resin composition was prepared by mixing 9,000 g of polypropylene (HYPOL B200, manufactured by Mitsui Petrochemical Industries, Ltd., Melt flow rate: 0.5 g/10 min. measured by the method shown in ASTM D1238), 500 g of polycarbonate (Lexan 101, manufactured by General Electric), and 500 g of polypropylene modified with maleic anhydride (graft modification with maleic anhydride: 3% by weight).

The resulting resin composition was fed to a blown film extrusion machine (manufactured by Toshiba Machine Co., Ltd.) to extrude a film of 30 μm thick at 240° C. The film was then stretched in machine direction to 6.6 times its length at 135° C. with a hot plate, and the stretched film was split with a wire fillet roll into net-like split yarns. The resulting split yarns were charged by feeding the split yarns between corona discharge electrodes disposed at an interval of 8 mm with a voltage applied of 9 kV (direct current) for residential period of 0.5 sec., and wound on a paperboard cylinder. The process comprising the step of blown film extrusion through the step of winding on the paperboard cylinder was continued for a predetermined period (five hours). When the stretched film was split with the needle-mounted roll, the resulting split yearns were often because the yearns were fine. As a result, the split yearns were wound on the needle-mounted roll and then the film itself was by tension. The frequency of film tear caused by tension is shown in Table 1. The thus treated split yarns were cut into split fibers of 90 mm, and treated with an opener to produce a raw cotton of electret fibers.

The electret fiber raw cotton was fed to a web forming machine to form a web, which was then needle punched to produce an electret filter having a deposition weight of 100 g/m² and a thickness of 2 mm. The frequency of film tear caused by tension during the production is shown in Table 1.

The resulting electret filter was evaluated for its collection efficiency in accordance with the procedure as described below. The results are also shown in Table 1.

EVALUATION OF COLLECTION EFFICIENCY

The collection efficiency was evaluated with an evaluation apparatus schematically illustrated in FIG. 1.

First, NaCl particles having a particle size of 0.3 μm produced in an aerosol generator 1 (manufactured by Japan Science Industries K. K.) were fed to a chamber 3 together with a clean air which had passed through an air filter 2. When NaCl particle concentration in the chamber 3 reached a constant level of from 2 to $6 \times 10^6$ (particles/ft$^3$), a blower 4 was actuated to start aspiration of the gas within the chamber 3 through a flow path 5 with the flow rate being regulated by a flow rate-regulating valve 6. In the flow path 5 was provided an electret filter 8 to be evaluated. Flow rate of the gas was measured with a flowmeter 7. When the flow rate reached a constant level of 0. 5 m/sec., concentration $C_{in}$ and concentration $C_{out}$ of the NaCl particles in the upstream side and downstream side of the electret filter 8 were measured with particle counters 9a and 9b (KC-01A, Rion K.K ), respectively.

The collection efficiency was calculated by the following formula:

Collection efficiency = $[1 - (C_{out}/C_{in})] \times 100(\%)$

COMPARATIVE EXAMPLE 1

The procedure of Example 1 was repeated except that the film extruded and stretched as in Example 1 was subjected to the homo charging before the splitting of the film into the split yarns. The frequency of the film tearing as well as the collection efficiency of the resulting electret filter were evaluated as in Example 1. The results are shown in Table 1.

TABLE 1

|  | Frequency of film tearing* | Collection efficiency, % |
|---|---|---|
| Example 1 | 0 | 65.2 |
| Comparative Example 1 | 5 | 67.0 |

*in five hours.

In the method of the present invention, the homo charging is carried out after the splitting of the film. Therefore, the film does not suffer from decreased film strength due to the oxidation of the film surface or formation of minute surface irregularities caused by the homo charging as in the conventional process wherein the homo charging is carried out before the splitting of the film, and consequently, the film is less likely to be torn during the production leading to reduced production troubles such as winding of the torn film onto rolls and the like. Accordingly, the method of the present invention enables a reliable, highly efficient, and quick production of an electret filter having various excellent performances including the collection efficiency with no production troubles as found in the prior art processes.

We claim:

1. A method for producing an electret filter comprising the steps of
forming a film comprising a high molecular weight resin material,
wherein said high molecular weight resin material is a compound selected from the group consisting of a non-polar high molecular weight compound, a polar high molecular weight compound and a non-polar high molecular weight compound modified by graft polymerization and mixtures thereof,
splitting the film to form split yarns,
subjecting the split yarns to a homocharging, and
producing the electret filter from the charged split yarns.

2. A method for producing an electret filter comprising the steps of forming a film comprising a high molecular weight resin material,
wherein the resin material comprises in weight ratio 60 to 99 parts of a non-polar high molecular weight compound,
0.5 to 39.5 parts of a polar high molecular weight compound, and
0.5 to 20% by weight of a non-polar high molecular weight compound modified by graft polymerization,
splitting the film to form split yarns,
subjecting the split yarns to a homocharging and producing the electret filter from the charged split yarns.

3. A method according to claim 1 wherein said modified non-polar high molecular weight compound is a non-polar high molecular weight compound which is graft copolymerized with at least one compound selected from unsaturated carboxylic acids and their anhydrides.

4. A method according to claim 3, wherein said graft modified non-polar high molecular weight compound contains from 0.05 to 15% by weight of the unsaturated carboxylic acid or the derivative thereof.

5. A method according to claim 3, wherein said unsaturated carboxylic acids and their derivatives are unsaturated dicarboxylic acid and their anhydrides.

6. A method according to claim 5 wherein said unsaturated dicarboxylic acids and their anhydrides are at least one compound selected from maleic acid, nadic acid, and their anhydrides.

7. A method according to claim 1, wherein said high molecular weight resin material comprises a mixture of a non-polar high molecular weight compound and a polar high molecular weight compound in a weight ratio of the non-polar compound to the polar compound of 60 to 99:0.5 to 39.5.

8. A method according to claim 7 wherein said resin material contains the polar high molecular weight compound and 0.5 to 20% by weight of a non-polar high molecular compound modified by graft polymerization.

9. A method according to claim 1, wherein said film is formed to have a thickness of 10 to 100 μm.

10. A method according to claim 1, wherein said film is stretched to 5 to 10 times its length before the splitting step.

11. A method according to claim 2 wherein said graft modified non-polar high molecular weight compound is modified by graft copolymerization with an unsaturated dicarboxylic acid, an unsaturated dicarboxylic acid anhydride, or a mixture thereof.

12. A method according to claim 2 wherein said graft modified non-polar high molecular weight compound contains 0.05 to 15% by weight of the unsaturated dicarboxylic acid, unsaturated dicarboxylic acid anhydride, or mixtures thereof, based on the weight of the modified non-polar high molecular weight compound.

13. A method according to claim 11 wherein said unsaturated dicarboxylic acids and their anhydrides are selected from the group consisting of maleic acid, nadic acid and their anhydrides.

14. A method according to claim 2 wherein said film is formed to have a thickness of 10 to 100 $\mu$m.

15. A method according to claim 2, wherein said film is stretched 5 to 10 times its length before splitting.

* * * * *

UNITED STATES PATENT AND TRADEMARK OFFICE
CERTIFICATE OF CORRECTION

PATENT NO. : 5,246,637
DATED : Sep. 21, 1993
INVENTOR(S) : Satoshi Matsuura; Akira Yokoyama; Yoshio Shinagawa It is certified that error appears in the above-indentified patent and that said Letters Patent is hereby corrected as shown below:

TITLE PAGE
[30] Foreign Application Priority Data, delete "3-100765"

and substitute therefor --3-100754--.

Signed and Sealed this

Thirty-first Day of May, 1994

Attest:

BRUCE LEHMAN

Attesting Officer     Commissioner of Patents and Trademarks